United States Patent [19]

Lundgren

[11] 4,073,663
[45] Feb. 14, 1978

[54] METHOD AND APPARATUS FOR AUTOMATIC BACTERIOLOGICAL CLEANING AND DISINFECTION OF OBJECTS

[76] Inventor: Ernst Harry Lundgren, Norra Grangesbergsgatan 11, S-214 50 Malmo, Sweden

[21] Appl. No.: 688,360

[22] Filed: May 20, 1976

[30] Foreign Application Priority Data

May 20, 1975 Sweden .............................. 7505691

[51] Int. Cl.$^2$ .............................................. B08B 3/02
[52] U.S. Cl. .......................................... 134/10; 21/80;
134/18; 134/29; 134/30; 134/56 R; 134/60;
134/68; 134/72; 134/107
[58] Field of Search .................... 134/10, 18, 29, 30,
134/32, 60, 68, 72, 107, 56 R, 56 D; 21/80

[56] References Cited

U.S. PATENT DOCUMENTS

| | | | |
|---|---|---|---|
| 890,251 | 6/1908 | Thompson | 134/68 X |
| 2,619,097 | 11/1952 | Von Brömssen | 134/60 X |
| 2,633,437 | 3/1953 | Detjen | 134/30 X |
| 2,947,311 | 8/1960 | Fox et al. | 134/72 X |
| 3,849,197 | 11/1974 | Sorrentino | 134/10 |

*Primary Examiner*—Richard V. Fisher
*Attorney, Agent, or Firm*—Berman, Aisenberg & Platt

[57] ABSTRACT

For automatic bacteriological cleaning and disinfection of objects there is provided a series of treatment compartments which can be closed individually. The objects are fed sequentially into the compartments. They are treated with fluid therein in a predetermined cycle of operations. Liquid used in one compartment is recovered and collected for use in another compartment in a following cycle of operations. In one operation, objects are moved from a first compartment to a second compartment, fresh treating liquid is pumped from a tank associated with the second compartment into that compartment, and then this liquid is discharged directly to another tank associated with the first compartment.

11 Claims, 9 Drawing Figures

METHOD AND APPARATUS FOR AUTOMATIC BACTERIOLOGICAL CLEANING AND DISINFECTION OF OBJECTS

BACKGROUND OF THE INVENTION

1. Field of the Invention

This invention relates to a method and an apparatus for automatic bacteriological cleaning and disinfection of objects.

More particularly the invention relates to a method of this type comprising sequential treating of the objects in compartments arranged one after the other for performing (during a cycle of operations) a sequential series of treatment operations, such as pre-flushing, washing, rinsing and drying. The objects are fed successively to the different compartments and are received by each compartment to be subjected to one of said operations therein, said operations of a cycle being performed simultaneously one in each compartment.

The invention also relates to an apparatus comprising a series of compartments, conveying means for feeding the objects sequentially to each of said compartments, and means for supplying treating medium to the objects when received by the different compartments.

2. Description of the Prior Art

Recently it has been found that the carriages used in hospitals or the like for transporting food from a central kitchen to patients in different hospital sections form a source for spreading bacteria and may be the cause of nosocomical infection. The same problem exists regarding the carriages used for transporting wash which may be seriously contaminated with bacteria from hospitals to central laundries.

So far the carriages used for the above purpose have been cleaned by methods which in no way meet the requirements of bacteriological cleaning set up for hospitals, and often the carriages have only been flushed manually with water. Since the carriages used for transporting food may reciprocate four times a day between the kitchen and the different hospital sections, it will be understod that bacteria collected on the carriages can be spread rapidly over a hospital in its entirety.

A prior-art apparatus for such cleaning and disinfection comprises a compartment in which the carriages are subjected to different treatment operations sequentially. First, the carriage is flushed and then it is sprayed by water containing a cleaner, possibly in combination with a physical treatment. When cleaner adhering to the carriage has been rinsed off, the carriage is dried. This type of apparatus is available both with open systems, i.e. liquid sprayed over the carriage is allowed to run off to a drainage, and closed systems, i.e. liquid sprayed over the carriage is collected to be used later.

The utilization of open systems has been preferred because bacteria, if any, which have collected in the water used in the different treatment steps follow the water entrained therein to the drainage. However, such systems are highly water and energy consuming because heated water is used in several treatment steps and is allowed to escape to the drainage. On the contrary, when closed systems are used considerably less water and energy is consumed but a great drawback is that bacteria washed off the carriage will collect in the water used at the different treatment steps whereby the cleaning effect deteriorates as the apparatus continues in operation. This prior art apparatus also has the drawback that only one carriage at a time can be cleaned and, therefore, the cleaning is time consuming.

Another prior art apparatus which has a larger capacity than that described above comprises a passage in which the carriages to be cleaned are fed continuously and, during such movement, are subjected to the different cleaning operations: pre-flushing, spraying with water containing a cleaner, rinsing and drying. This apparatus, too, is available with either closed or open systems, and, therefore, has the same drawbacks associated therewith as the apparatus described above. Moreover, in an apparatus of this type the use of open systems is not fully reliable from a bacteriological point of view because the carriage is moving during the different treatment operations whereby bacteria can be thrown or may flow together with the liquid used at the treatment from one end of the carriage to another in the feed direction of the carriage and thus can escape the cleaning action.

SUMMARY OF THE INVENTION

A primary object of the invention therefore is to provide method and apparatus for effective bacteriological cleaning and disinfection of objects.

It is a further object of this invention to provide new and improved method and apparatus for automatic cleaning of objects wherein the treating medium to the least possible extent is transferred from one compartment to another in order to minimize the risk of bacteria being spread during the cleaning of objects in the compartments.

A still further object of this invention is to provide new and improved method and apparatus for automatic cleaning of objects, which are economical in operation by recovering and reusing cleaning and rinsing liquid used in the different compartments, and heat energy contained therein.

Another object of this invention is to provide new and improved method and apparatus for automatic cleaning of objects which allow the objects to be fed successively through a row of treatment compartments and the objects received by a compartment to be treated separated from objects in adjacent compartments.

Yet another object is to provide a new and improved method and apparatus for effective and economical bacteriological automatic cleaning and disinfection of carriages, such as are used for transporting food and wash in hospitals, at the exterior and interior surfaces thereof while maintaining the carriages in their normal position.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the method of this invention for automatic bacteriological cleaning and disinfection of objects by sequential treating of the objects in compartments arranged one after the other comprises the steps of feeding the objects stepwise to each of the compartments; closing each of the compartments to the surroundings and to the adjacent compartments in a liquid-tight manner; treating the objects received by the compartments in a cycle of operations comprising a sequential series of treatment operations by fluid supplied to the compartments, one operation being performed in each compartment; recovering and collecting predetermined quantities of the fluids used in later treatment operations of the cycle; reusing the quantities of fluids thus recovered and collected, in at least one earlier operation in a following cycle of operations; and supplying fresh fluid to the rest of said fluids in said later operations.

The invention also provides apparatus for working said method comprising a row of compartments; means for providing liquid-tight closure of each compartment relative to the surroundings and to adjacent compartments; conveying means confined to each compartment for moving objects to, through and out of the compartment; tanks for holding treatment fluid individually for each compartment; means for supplying such treatment fluid to each of said compartments; means in each compartment for distributing the fluid over the objects received therein; means for controlled transfer of a predetermined quantity of fluid for one compartment to the tank for another compartment; and means for supplying fresh fluid to the rest of the fluid for said one compartment.

Preferably the cycle of operations comprises pre-flushing, washing, rinsing and drying, predetermined quantities of the fluids used for washing and rinsing being recovered and collected to be used in the pre-flushing operation during a following cycle.

It is also preferred to have the temperature of the fluid used for the washing operation kept lower than the temperature of the fluid used for the rinsing operation and higher than the temperature of the fluid used for the pre-flushing operation.

It is also preferred to have fresh liquid (replacing liquid recovered and collected for use in a following cycle) supplied in heat exchange relationship with the liquid used in at least one of the operations of a cycle.

The accompanying drawings, which are incorporated in and constitute a part of this specification, illustrate embodiments of the invention and, together with the description, serve to explain the principles of the invention.

Reference will now be made in detail to the present preferred embodiments of the invention, examples of which are illustrated in the accompanying drawings.

DESCRIPTION OF THE PREFERRED EMBODIMENTS

The method according to the invention for automatic cleaning and disinfection of objects is described below with reference to the embodiment shown in FIGS. 1 to 4 of a preferred apparatus for handling carriages in working the method according to the invention. However, although the invention will be described with reference to the cleaning and disinfection of carriages, such as are used in hospitals and the like for transporting, for instance, food between a central kitchen and different sections of the hospital, it will be clear from the description which follows that the general concept of the invention can be utilized in any other application where cleaning of a plurality of substantially identical objects is required.

Figure 1:
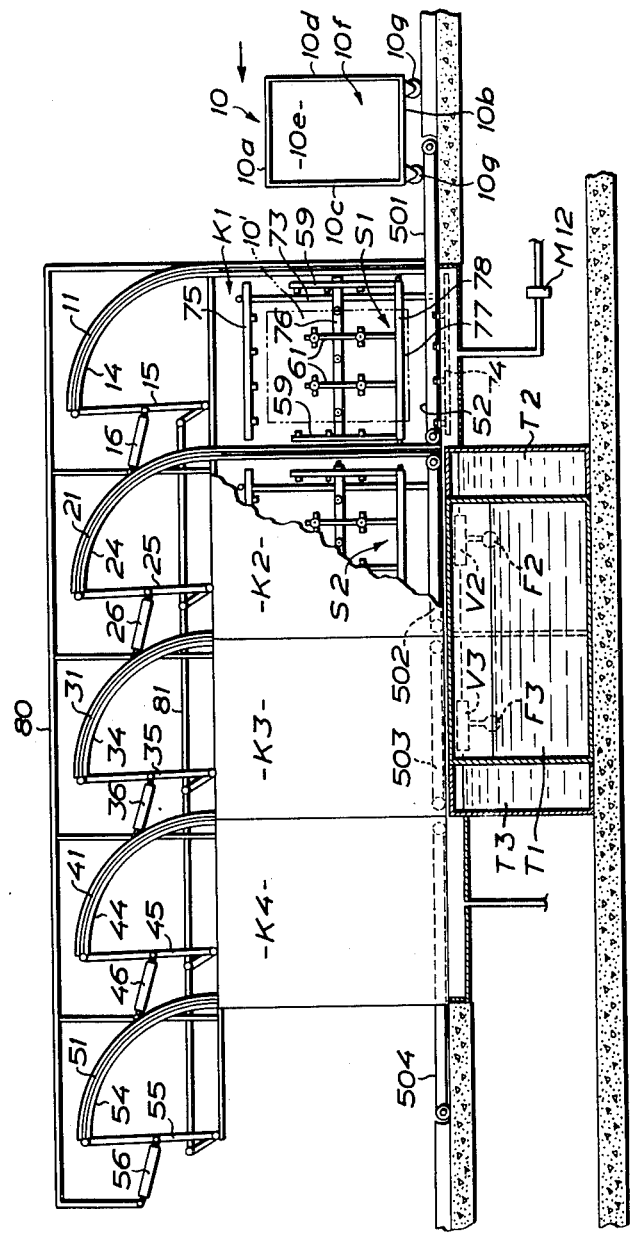
FIG. 1 is a side view, partly a longitudinal sectional view taken along line I—I in FIG. 3, of a preferred embodiment of an apparatus for automatic cleaning of objects, such as carriages, by the method according to the teachings of the invention.

As will be seen from FIG. 1 the cleaning apparatus shown therein comprises four parallelepipedic compartments K1 to K4 arranged in a linear row one after the other in through communication with each other. The apparatus is constructed for handling carriages of the type shown at 10 in FIG. 1, which comprises a box-like structure open at one side thereof and including top and bottom walls 10a and 10b, respectively, end walls 10c and 10d, and a rear wall 10e the walls bounding a cavity 10f which is available through the open side of the carriage. The carriage runs on wheels 10g.

The carriages are fed through the apparatus from the inlet end thereof (to the right as seen in FIG. 1) to the outlet end (to the left as seen in FIG. 1) as indicated by an arrow in FIG. 1 passing sequentially through the compartments which are arranged as a pre-flushing compartment K1, a washing compartment K2, a rinsing and disinfection compartment K3, and a drying compartment K4. The compartments are each adjusted to the carriages as to width, length and height.

Compartments K1 to K4 are arranged with their lower portions on a level with a surrounding floor and comprise side walls and bottoms interconnected in the longitudinal direction of the apparatus, and individual tops. Sills are provided between the bottoms, each of which slopes toward an individual drain.

Walls 11, 21, 31, 41, 51 of the compartments K1 to K4 (each extending perpendicularly to the feed direction) comprise two mutually-spaced interconnected wall elements 12, 13 which can be displaced up and down. The wall elements are separately guided in guide rails 14, 24, 34, 54 arranged vertically at the inner side of the longitudinal sides of the apparatus and extending upwardly in a bow beyond the tops of the compartments.

The double walls associated with each compartment are pivotally connected at their upper ends to pairs of arms 15, 25, 35, 45, 55, respectively, pivoted to the top of the compartment. Between each pair of arms and a frame 80 on the tops of the compartments there is provided a pneumatic power cylinder 16, 26, 36, 46, 56 for moving the associated pair of walls up and down. The arms are interconnected at least at one side of the apparatus by a link 81 to insure a synchronous movement when the walls are pulled up to their upper positions and are pushed down to their lower positions.

When the walls are in their lower positions the compartments are thus separated from each other and from the surrounding by double walls to insure that, during the operation of the apparatus, liquid used in one compartment cannot arrive in other compartments. Accordingly contaminants, including bacteria, if any, cannot be transferred, for instance, by splashing from one compartment to an adjacent compartment. The sills located between the compartments — one sill being shown at 88 in FIG. 4 — are designed to project between the wall elements when the double walls are in their lower positions and thus contribute to a satisfactory sealing between adjacent compartments.

Guide rails 14, which are preferably made of tetrafluorethylene, provide a satisfactory liquid-tight seal against the movable walls. These walls can be made as integral flexible plastic or metal sheets or may be composed of a plurality of hinged segments or the like providing a liquid-tight wall.

A conveyor belt system (extending through the compartments and comprising one section 501, 502, 503, 504, respectively, for each compartment) is provided on the floor of the apparatus. It will be seen that conveyor sections 501 and 504 at the inlet end and the outlet end project from the associated compartment, conveyor sections 502 and 503 being of a length which is limited to the length of the associated compartments. Individual conveyors in each of the compartments are advantageous over a single conveyor extending continuously through the several compartments from one end of the apparatus to the other end thereof since they avoid transferring contaminants from one compartment to another. Drive means, not shown, are provided for driving the conveyor sections synchronously and at intervals in one and the same direction for feeding the apparatus, the conveyor system and the carriages being arranged for interengagement in order to couple the carriages to the individual conveyors and to drive them in dependence on the movement thereof. The carriages run with their wheels on rails 52 arranged on the bottoms of the compartments.

In compartments K1 to K3 there are arranged flushing means S1 to S3 identical to each other for spraying the carriages with pressurized water or other liquid for suitable treatment of the carriages.

Figure 3:
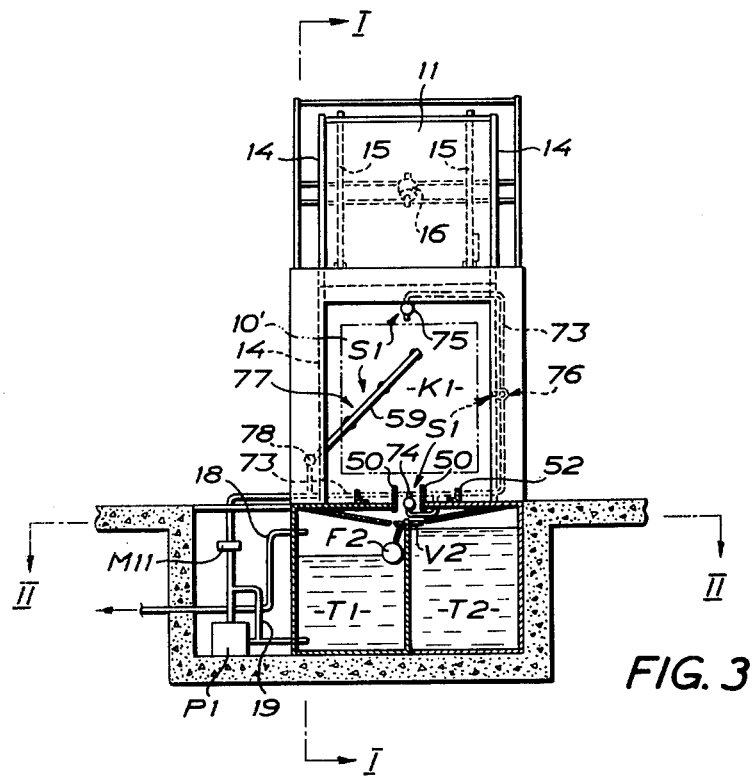
FIG. 3 is an end view of the apparatus as seen from the inlet end thereof the space located below the compartments being shown in cross-section along line III—III in FIG. 2.
Figure 4:
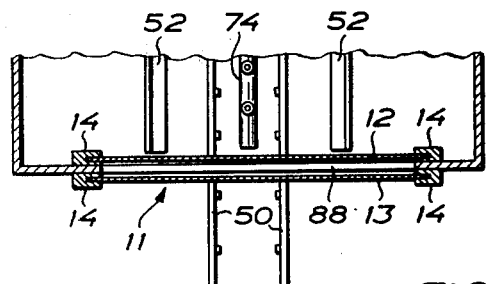
FIG. 4 is an enlarged fragmentary cross-sectional view seen from above and showing guide rails for the movable walls of the compartments.

A preferred embodiment of such means S1 is clearly shown in FIGS. 1 and 3 in pre-flushing compartment K1. A supply tube 73 for liquid is connected to flush tubes 74 and 75 arranged at the compartment bottom and top, respectively, and extending in the feed direction of the carriages, i.e. the longitudinal direction of the apparatus, and to flush members 76, 77 at the side walls of the compartment, one of said members comprising a horizontally-arranged flush tube extending in the feed direction and rotatable back and forth about the axis thereof over a predetermined arc. Flush member 77 arranged at the side wall opposite to flush tube 76 comprises a planar or flat frame pivotally mounted at said side wall to swing over a predetermined arc about a horizontal hollow shaft 78 arranged as a liquid supply manifold. The frame comprises, in addition to horizontal hollow shaft 78, also two parallel outer flush tubes 59 arranged at the ends of the manifold, and two inner flush tubes 61 parallel to each other and to tubes 59, which are arranged between tubes 59. Tubes 61 are shorter than tubes 59 to be introduced into cavity 10*f* of carriage 10 for scanning the interior sides thereof at the reciprocating movement of the frame over a predetermined arc while tubes 59 scan the front and back sides 10*c* and 10*d*, respectively, of the carriage. The relationship of the flushing means and the carriage is indicated in FIGS. 1 and 3 where the contour of the carriage is shown by dash-and-dot lines 10'. The flushing means can of course be designed in another way if preferred for cleaning other objects than carriages of the type described having a cavity available through a side opening.

Flush tubes 59 and 61 have nozzles equally spaced over the length thereof for spraying pressurized liquid uniformly over the respective sides of the carriage when the tubes are scanning said sides, the number and position of the nozzles being arranged in such a way that every part of the surfaces of said sides can be covered by liquid. The outer flush tubes 59 of the frame have three nozzles directed towards the centre of the compartment, the inner flush tubes 61 having nozzles directed at right angles to the flush tubes and to each other as well as a nozzle at the outer end of each tube directed in the extension thereof.

Flush tubes 74 and 75 at the bottom and the top, respectively, of the compartment preferably are stationary but they can be pivoted if required for bacteriological reasons.

Under the bottoms of the compartments there is a space which houses tanks for different liquid fluids which are heated individually to predetermined temperatures and are maintained individually at said temperatures by separate hot water loops. Furthermore, there are means for controlling the liquid flow, as well as other control means required for the operation of the apparatus.

Figure 2:
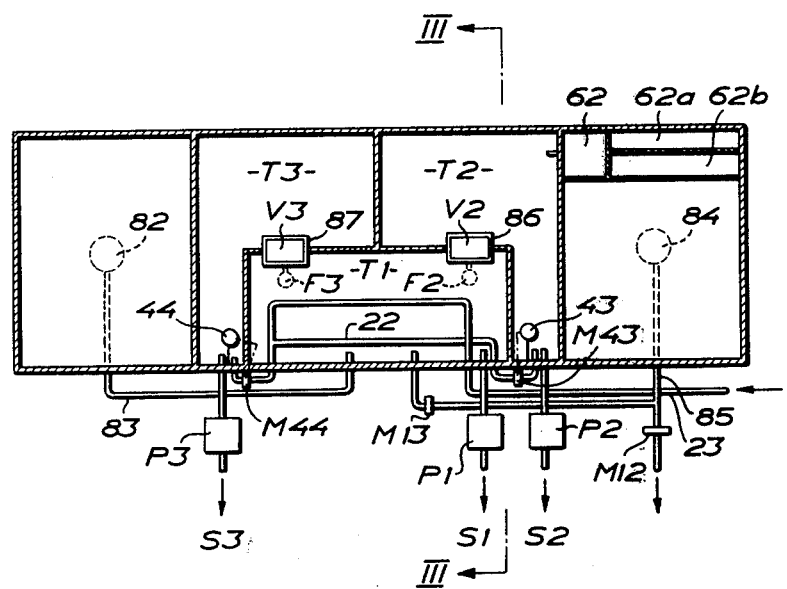
FIG. 2 is a horizontal sectional view taken along line II—II in FIG. 3 of the apparatus in FIG. 1.

FIG. 2 discloses a preferred disposition of the space located below the bottoms of the compartments.

A tank T1 for containing liquid to be used for an initial flushing of the carriages extends along a portion of the side of the apparatus and is connected via a pump P1 to conduit 73 of flushing means S1 provided in pre-flushing compartment K1. The liquid in tank T1 contains a cleaner and is maintained at a temperature of about 35° C. The temperature of the liquid to be used for the pre-flushing of the carriages preferably is selected to about 35° C to be safely below the temperature range from 40° to 60° C at which proteins coagulate. Since the carriages can have food particles and other waste material adhering thereto, temperature conditions for coagulating any proteins in this waste material are preferably avoided since coagulated proteins would impair the washing effect of the flushing. Tank T1 also has an overflow protection 18 connected to the local drainage system.

A tank T2 disposed partially inwardly of tank T1 is connected via a pump P2 to conduit 73 of flushing means S2 arranged in washing compartment K2. Tank T2 is intended for liquid containing a cleaner, which can be supplied by pump P2 to the flushing means in compartment K2 and can be sprayed evenly over a carriage located therein. The temperature of the liquid in tank T2 is maintained at a suitable value in the range from 40° to 60° C.

The cleaner is supplied to the liquid in tank T2 by means of a separate dosing means 62 and may comprise any suitable detergent combined with a wetting agent whereby the run-off of the liquid sprayed onto the carriage will be facilitated.

A third tank T3 disposed partially inwardly of the tank T1 symmetrically to tank T2 is connected at one side of the apparatus to conduit 73 of flushing means S3 in the washing and disinfection compartment K3 via a pump P3. The liquid in tank T3 is maintained at a temperature of about 85° C. When the apparatus is operating, this liquid is supplied by pump P3 to flushing means S3 in compartment K3 for washing and disinfection of a carriage located therein. The temperature of 85° C of the liquid in tank T3 is not critical; this value is chosen because washing by means of liquid at this temperature provides a good disinfecting action. The liquid can possibly be at a higher temperature, if required, sometimes a lower temperature may be sufficient for insuring satisfactory disinfection.

Contrary to compartments K1 to K3 drying compartment K4 is provided with means S4 for uniform distribution of hot air from an aggregate (not shown) over a carriage (located in this compartment) for drying the carriage. Such distribution means S4 may be constructed basically in the same manner as the flushing means provided in compartments K1 to K3. However, the nozzles should be of a construction suitable for air. The drying means comprises filters (not shown) for removing solid material and bacteria from the hot air supplied to compartment K4.

Furthermore, the bottom of drying compartment K4 is constructed for collecting water running off the carriage as well as condensate which is supplied through a drain 82 and a conduit 83 to tank T1.

A drain 84 in compartment K1 is connected by a conduit 85 to tank T1 and to the local drainage system or the like. Solenoid valves M12 and M13 are provided in conduit 85 for the control of the communication from drain 84 to the local drainage system and tank T1, respectively.

A drain 86 in compartment K2 is connected to tanks T1 and T2 via a valve V2.

A drain 87 in compartment K3 is connected to tanks T1 and T3 via a valve V3.

In the embodiment shown in FIGS. 1 to 4 tanks T1 to T3 are disposed below the bottom of compartments K2 and K3, drains 86 and 87, respectively, from said compartments providing a direct communication to tanks T2, T1 and T3, T1, respectively, via valves V2 and V3, respectively, which comprise, in the illustrated embodiment, rotatable plates controlled by means of floats F2 and F3, respectively, positioned in tank T1. These valves are normally in a position for maintaining communication between the drain of compartments K2 and K3, respectively, and tanks T2 and T3, respectively.

Floats F2 and F3 operate to activate valves V2 and V3, respectively, when the liquid level in tank T1 has sunk to a predetermined height, to provide communication between the drains of the compartments and tank T1. Floats F2 and F3 are also arranged to activate pumps P2 and P3, respectively, when a predetermined level in tank T1 is sensed.

Floats F2 and F3 are individually adjustable so that they will activate valves V2 and V3, respectively, independently of each other at different liquid levels in tank T1. Moreover, floats F2 and F3 are arranged to switch valves V2 and V3, respectively, when the liquid level raises to a predetermined initial level in tank T1 so that communication between drain 86 of compartment K2 and tank T2 is opened while communication from this drain to the tank T1 is closed, and so that the communication between drain 87 of compartment K3 and tank T3 is opened while communication from this drain to tank T1 is closed.

The embodiment described above and shown in the drawing is a particularly simple and cheap construction for the distribution of liquid collected at the bottoms of compartments K2 and K3 to tanks T1 to T3. Other and more inventive constructions can, of course, be used, e.g. solenoid valves in case the tanks are disposed in remote spaces.

Tanks T2 and T3 have a supply conduit 23 for the supply of fresh liquid free from contaminants in order to compensate for drained off liquid. This supply conduit 23 forms a loop 22 in tank T1 for preheating of liquid supplied to tanks T2 and T3 by utilizing the surplus heat energy which has been supplied to the liquid in tank T1 by liquid of a higher temperature from compartments K2 and K3 when valves V2 and V3 are switch to connect the drains of compartments K2 and K3 to tank T1. Thereby also cooling of the liquid in tank T1 to a predetermined temperature will be obtained.

The supply of fresh liquid to tanks T2 and T3 is controlled by means of level sensors 43, 44 provided in the respective tanks, which are arranged to activate at a predetermined value solenoid valves M43 and M44 in branches of conduit 23 extending to tanks T2 and T3, respectively.

Dosing means 62 is arranged to supply from containers 62a and 62b holding detergent and wetting agent, respectively, fresh cleaner to tank T2 in proportion to the liquid drawn therefrom so that a constant concentration of cleaner will be maintained in tank T2.

When the apparatus is operated, carriages 10 are engaged with conveyor section 501 and are transferred one after the other to pre-flushing compartment K1 for a first treatment operation of a cycle of operations. Compartments K1 to K4 operate individually according to associated programs which initiate and terminate the operations therein. When a carriage 10 is introduced into compartment K1, all walls 11, 21, 31, 41 and 51 between the compartments are of course lifted to their upper positions to allow carriages in compartments K1 to K3 to be fed at the same time one step to the left into a following compartment and the carriage disposed in compartment K4 to be delivered from the apparatus. During the performance of the operations proper, all said walls are, however, in their lower positions.

The apparatus is started when the temperature of the water in each of the three tanks has attained its predetermined value. After three initiating cycles of operations, a fourth carriage is engaged with conveyor section 501, which carries the carriage one step forward, i.e. to a position in which it is located in pre-flushing compartment K1, the two carriages forwardly thereof at the same time being advanced each one step to the left into the following compartment and the leading carriage being delivered from the apparatus. The double walls of compartments K1 to K4 are then moved to their lower positions and then each compartment K1 to K4 operates during the continued cycle of operations in accordance with the program associated with the compartment in question.

Initially the pump P1 is started and supplies liquid from tank T1 to flushing means S1 of compartment K1, by which the liquid is sprayed over the carriage located in the compartment. This liquid removes solid and liquid material from the carriage and is allowed to escape to drain 84 where the solid material may be collected on a screen.

At the same time as pump P1 starts, the drying means S4 of the compartment K4 is put into operation and then operates during the entire cycle of operations.

When the level in tank T1 has sunk under the predetermined value associated with the respective floats F2, F3 the float in question switches the associated valve, V2 and V3, respectively, and pumps P2 and P3, respectively, are started. When either of pumps P2 and P3 is started, pump P1 is stopped or brought to idle. By the said switching of valves V2 and V3, there is opened a communication between drains 86 and 87 of compartments K2 and K3, respectively, to tank T1. Thereby, the cleaning liquid sprayed in compartment K2 over the carriage located therein will flow down into tank T1 from the drain of compartment K2 after having acted on the carriage, and the liquid sprayed in compartment K3 over the carriage located therein will flow down into tank T1 from the drain of the compartment K3 after having acted on the carriage therein. When the level in tank T1 has raised to the predetermined initial level, floats F2 and F3 operate to switch valves V2 and V3 to such position that communication will be obtained between drain 86 of compartment K2 and tank T2 and drain 87 of compartment K3 and tank T3, respectively, during the remaining part of the cycle of operations of the apparatus, whereby the liquid from tank T2 and T3 (sprayed over the carriage in question in compartments K2 and K3, respectively) is recirculated to the tanks T2 and T3, respectively.

The time invervals during which liquid is supplied to tank T1 from compartments K2 and K3 have a predetermined duration depending on the capacity of pumps P2 and P3 but will be limited finally by the activation of floats F2 and F3 at predetermined levels. The liquid sprayed in compartment K2 over the carriage located therein during the predetermined time interval removes nearly all contaminants remaining from the pre-flushing from the carriage. Since this liquid is allowed to drain off to tank T1 contaminants which — at the end of the predetermined time interval of continued spraying by means of cleaning liquid from tank T2 — are recirculated to this tank and are collected in said liquid, are at minimum.

In the same manner the liquid from tank T3 which is sprayed in compartment K3 over the carriage located therein during the initiating predetermined time interval of the cycle of operations rinses off nearly all liquid remaining on the carriage from proceeding treatment operations together with remaining contaminants, if any, and is supplied to tank T1 whereby a minimum of contaminants are collected in the liquid recirculated to tank T3 during the continued disinfecting treatment in compartment K3.

When pumps P2 and P3 are put into operation, the pump P1 is disconnected or, alternatively, a solenoid valve M11 (arranged in supply conduit 73 from pump P1 to flushing means F1 of compartment K1) interrupts the supply of liquid from tank T1 to compartment K1 whereby pump P1 idles, circulating the liquid in tank T1 in a shunt conduit 19. However, if suitable, pump P1 can be operated during the remaining part of the cycle of operations whereby solenoid valve M12 arranged in the connection between drain 84 of compartment K1 and the local drainage system is closed while a solenoid valve M13 in the connection between drain 84 and tank T1 is opened whereby the liquid in tank T1 can be recirculated from compartment K1 to tank T1.

When the programs associated with the different compartments have been run through, i.e. the carriages located in the different compartments have been subjected to satisfactory drying, disinfection, washing by spraying with cleaner and pre-flushing, pumps P2 and P3 are stopped as well as pump P1, it it was operating, the drying means is switched off, and all valves are switched for the preparation of a new cycle of operations.

Figure 9:
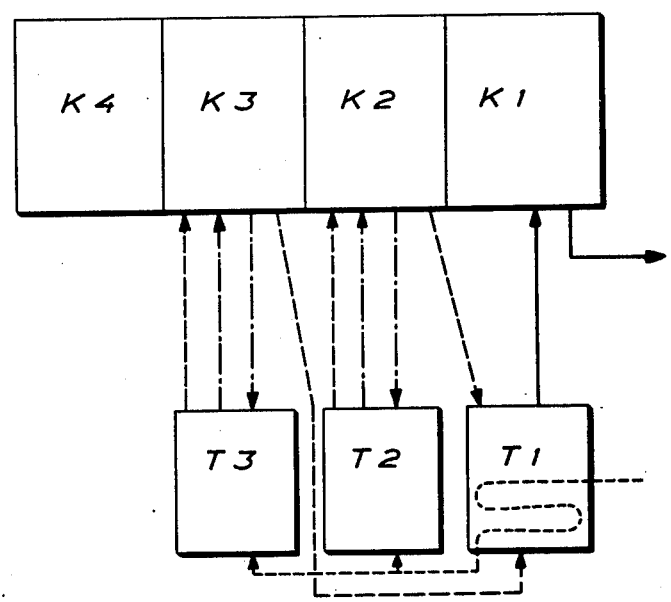
FIG. 9 is a flow chart illustrating a cycle of operations.

In summarizing the preferred method according to the teachings of the invention reference is made to FIG. 9.

During an initial step liquid is supplied to compartment K1 from tank T1 and discharged to the local drainage system as indicated by the solid flow lines.

During a following step liquid is supplied to compartments K2 and K3 from tanks T2 and T3, respectively, and is drained to tank T1 as indicated by the dashed flow lines.

During the final step liquid is circulated from tanks T2 and T3 to compartments K1 and K2 and returned therefrom to tanks T2 and T3, respectively, as indicated by the dash-and-dot flow lines.

Fresh liquid is supplied to tanks T2 and T3 in heat exchanging relationship to the liquid in tank T1, as indicated by dotted flow lines.

The apparatus as a whole is controlled by a timer in which all the functions and control events necessary for the operation of the apparatus are programmed.

The apparatus according to the invention is provided with means controlling critical procedures and interrupting the operation of the apparatus when malfunctions appear and indicating on an indication table where the failure is. Thus among others the temperatures in tanks T1 to T3 are controlled as well as the positions of the solenoid valves and the positions of the movable walls. If, for instance, a wall has not been moved to the lower position thereof at the beginning of a cycle of operations, this is indicated on the indication table, and the operation of the apparatus is stopped, whereby the fault arisen can be attended to. Consequently, there is obtained a complete check of the carriages having in fact been cleaned in a satisfactory manner by means of the apparatus.

The treatment or operating medium (liquid fluid) mentioned above in the description of the method and the apparatus according to the invention includes all types of liquid fluids, although water is the liquid preferred at present.

The method according to the invention makes it possible to save, during automatic cleaning and disinfection of objects, water and energy for heating the water in large quantities because in each cycle of operations only part of the water quantity used at the pre-flushing escapes to the local drainage system. The method and the apparatus according to the invention nevertheless obtain a cleaning and disinfection of treated objects which well meets the cleanliness and the bacteriological requirements for hospital use.

According to a further aspect of the invention the amount of liquid supplied to the drain from compartment K1 can be saved and can be purified in a suitable manner to be reused in the apparatus.

Furthermore, the liquid in compartment K3 can have an addition of disinfection agent, or a further compartment in which a disinfection agent in gas or liquid form is sprayed over the carriage may be arranged between compartment K3 and compartment K4.

Summarizing, it is an aspect of the method according to the invention that during a cycle of operations a medium acting on objects during an initial period is shifted from a later treatment step in the series of treatment steps to an earlier treatment step, and that the objects being treated without being cooled are successively heated during succeeding cycles of operations, whereby an utilization of the heat energy supplied during the method is achieved. Furthermore, the larger quantity of heat in the water contained in tanks T3 and T2 can be saved, when collected in tank T1, by preheating the fresh liquid supplied to tanks T2 and T3. The different treatment operations are performed in closed compartments, whereby the spreading of contaminants and existing bacteria, if any, by splashing is avoided.

Figure 5:
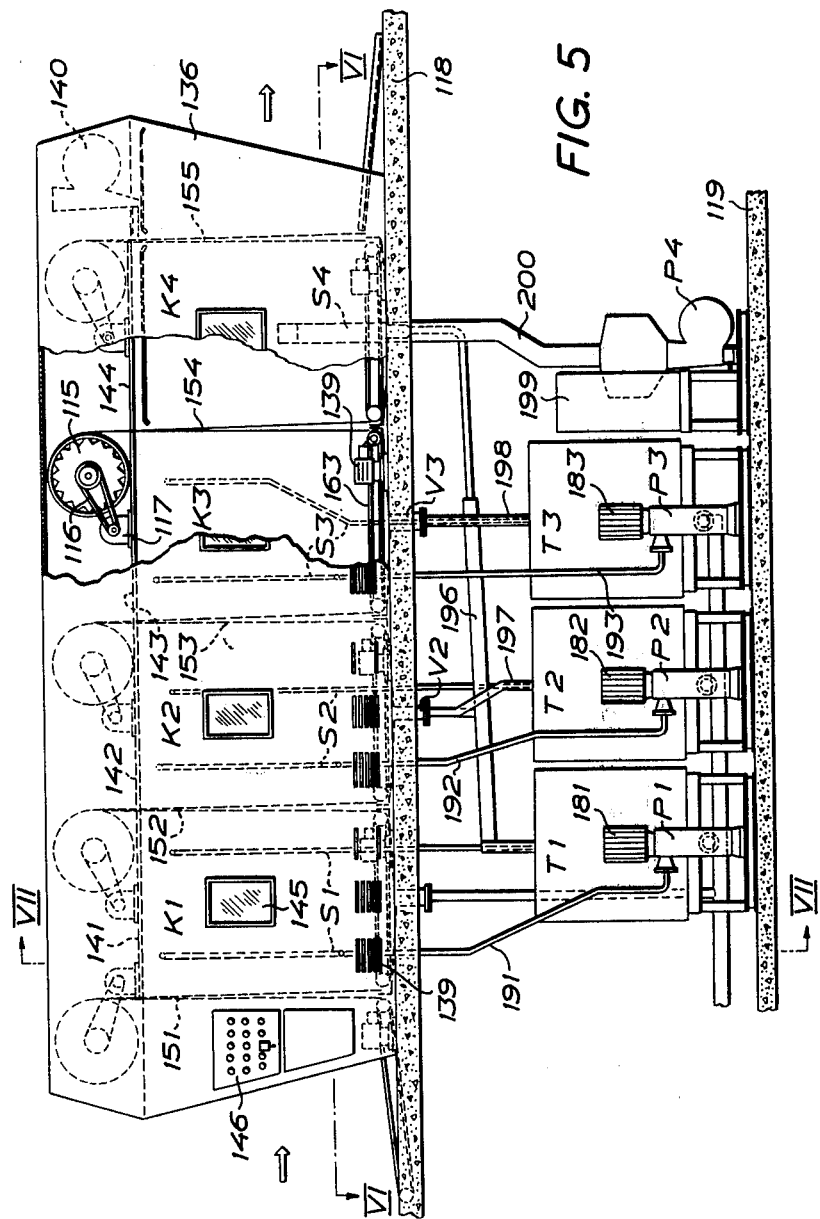
FIG. 5 is a side view, partly a longitudinal sectional view of a second embodiment of the apparatus according to the teachings of the invention.
Figure 6:
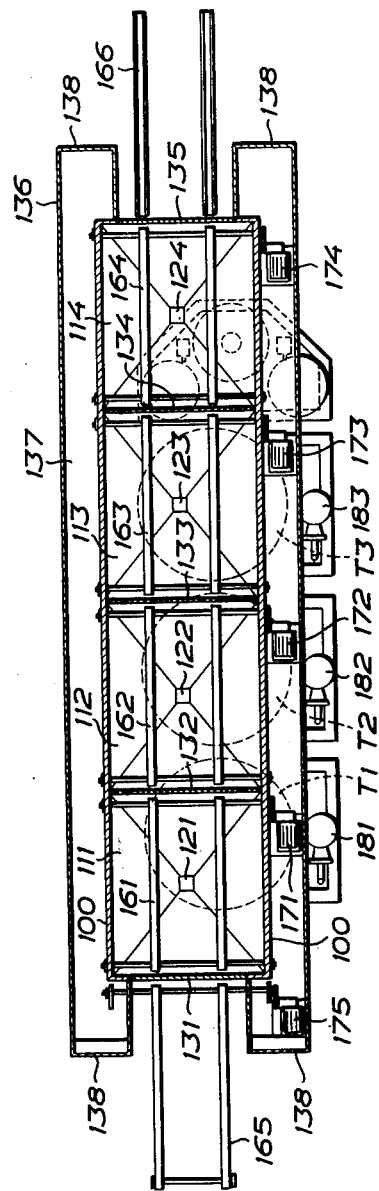
FIG. 6 is a sectional view along line VI—VI in FIG. 5.
Figure 7:
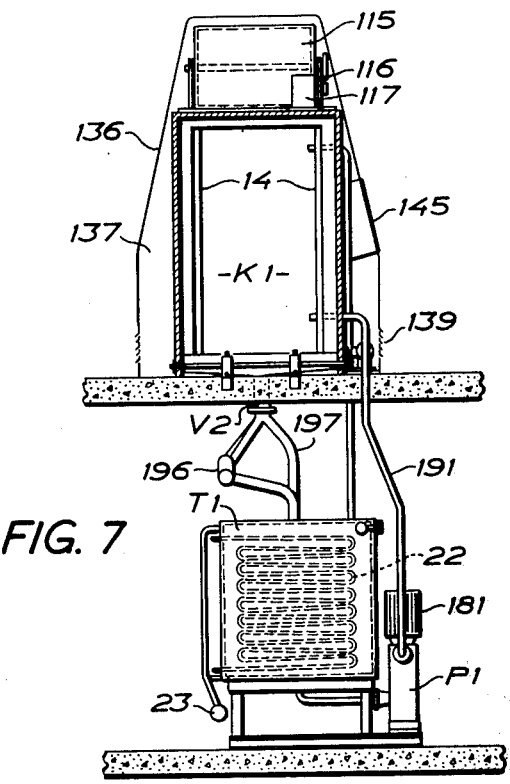
FIG. 7 is a sectional view along line VII—VII in FIG. 5.

The embodiment shown in FIGS. 5 to 8 provides compartments K1 to K4 in a steel sheet cabinet comprising continuous side walls 100, individual bottoms 111, 112, 113, and 114, each sloping towards a central drain 121, 122, 123, and 124, respectively. Between the compartments and at the ends of the row of compartments there are bottom sills 131, 132, 133, 134, and 135. The compartments have individual tops 141, 142, 143, and 144 and are provided with vertically movable walls 151, 152, 153, 154, and 155 in the manner described with reference to FIGS. 1 to 4, and these walls may be constructed and guided as previously described. Guide rails are indicated at 14, FIG. 7. However, a modified drive for the movable walls is shown in FIGS. 5 and 7. The drive of compartment K3 in FIG. 5 comprises a drum 115 rotatably mounted in any suitable way on the top of compartment K3 and connected by a chain or belt transmission 116 to an electric motor 117. The associated wall 154 is connected to the drum and is raised and lowered by the rotation of the drum, the wall being rolled on and off, respectively, during such movement. The drives for the other compartments are identical.

For the transport of carriages 10 (FIG. 1) through the apparatus each compartment has a bottom conveyor 161, 162, 163, and 164, and there is also an inlet conveyor 165, each connected to an electric drive motor 171, 172, 173, 174, and 175, respectively. The inlet conveyor rises progressively from the floor, indicated at 118, on which the apparatus is supported to the level of bottom 111 in compartment K1. Sloping outlet rails 166 are provided at the outlet of compartment K4.

Figure 8:
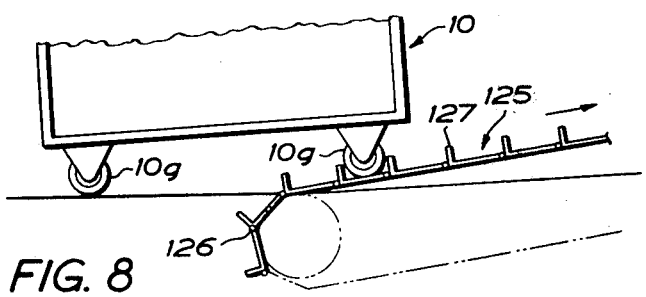
FIG. 8 is a fragmentary enlarged side view illustrating means for coupling a carriage to a conveyor chain.

Each conveyor comprises two endless chains which may be guided and driven in any suitable manner and which are arranged at a mutual distance corresponding to the wheel distance of the carriages. As shown in FIG. 8 each conveyor chain comprises L-shaped links 125 pivoted to each other at 126 and having one limb 127 projecting from the chain. As will be seen in FIG. 8 carriage 10 may be rolled onto the conveyor chain to be engaged therewith at the wheels which are received between adjacent limbs 127. The length of the links is adjusted to the wheel base of the carriage so that both wheel pairs can be engaged with the two chains between adjacent limbs in the manner shown in FIG. 8 for one wheel. In this case the wheels do not run on rails but are held stationary on the conveyors. However, suitable supports must be provided for the runs of the conveyor chains (the upper run) which support the carriages during the movement thereof through the apparatus.

Flushing means S1, S2, S3, and S4 are provided in the compartments and are shown diagrammatically only in FIGS. 5 to 7. Such means may be of the same construction as that described with reference to FIGS. 1 to 4 or of any other suitable construction.

The compartments are enclosed by a metal sheet housing 136 spaced from the side walls and tops of the compartments to form a surrounding passage 137. This passage is closed at the ends by end walls 138 and is connected to the surrounding at openings 139. A fan is provided as indicated at 140 to draw air through the passage between the housing and the compartments in order to maintain a low outside temperature on the apparatus. Windows 145 are provided in order to enable the operator to check the operation of the apparatus in the different compartments thereof. A control and indication panel 141 is provided on housing 136.

Tanks T1, T2, and T3 disposed on a lower floor level 119, are connected to their associated pumps P1, P2, and P3. The pumps are connected to electrical drive motors 181, 182, and 183 and are connected to their associated flushing means by conduits 191, 192, and 193, corresponding to conduit 73 in the embodiment of FIGS. 1 to 4. Drain 121 is connected to tank T1, and drains 122, 123 and 124 are connected to a common drain conduit 196, which communicates with tank T1. Additionally, drains 123 and 124 are connected by separate conduits 197 and 198, respectively, to tanks T2 and T3, respectively. Valves V2 and V3 are provided to control the communication between drains 122 and 123, respectively, and tanks T1 to T3 in the manner described with reference to FIGS. 1 to 4, and there are also provided necessary elements, such as floats and further valves, timers, dosing means, etc., for operating the apparatus in FIGS. 5 to 8 in accordance with the method described above with reference to FIGS. 1 to 4. In FIG. 7 the fresh water conduit is indicated at 23 and the loop in tank T1 for preheating of the fresh water, at 22.

P4 indicates a fan for supplying air to compartment K4, and associated with this fan is a heating and filtering apparatus 199 of any suitable type. A conduit 200 connects fan P4 with hot air distribution means S4 of compartment K4.

The apparatus disclosed in FIGS. 5 to 8 represents the presently preferred embodiment of the apparatus according to the teachings of the invention for working the method of the invention, the preferred form of which was described with reference to FIGS. 1 to 4.

It will be apparent to those skilled in the art that various modifications and variations could be made in the method and apparatus of the invention without departing from the scope or spirit of the invention.

I claim:

1. In a method for automatic bacteriological cleaning and disinfecting of objects by sequential treatment of the objects in separate liquid-tight compartments, the sequential steps comprising:
 a. pumping treating liquid from a first tank to contact objects in the first of a series of the liquid-tight compartments and then discharging the liquid so pumped;
 b. moving the objects from the first of said compartments to an intermediate liquid-tight compartment;
 c. supplying fresh treating liquid to a second tank;
 d. pumping the fresh treating liquid from the second tank to contact objects moved from the first of the series of liquid-tight compartments into the intermediate liquid-tight compartment and then discharging the liquid so pumped directly to the first tank;

e. moving the objects from an intermediate liquid-tight compartment into a final liquid-tight compartment; and f. drying the objects in the final liquid-tight compartment.

2. A method according to claim 1 for automatic bacteriological cleaning and disinfection of objects by sequential treating of the objects in compartments arranged one after the other comprising the steps of moving the objects stepwise to each of the compartments; closing each of the compartments to the surrounding and to adjacent compartments in a liquid-tight manner; treating the objects received by each compartment in a cycle of operations comprising a sequential series of treatment operations by fluid supplied to the respective compartments, one operation being performed in each compartment; recovering and collecting predetermined quantities of the liquids used in later treatment operations of the cycle; reusing the quantities of liquids thus recovered and collected, in at least one earlier operation in a following cycle of operations; and supplying fresh liquid to the rest of said liquids in said later operations.

3. A method as claimed in claim 2 wherein said recovering and collecting a predetermined quantities of the liquids used in said later treatment operations is performed during an initial part of such operations, the remaining liquid being circulated through the associated compartment during the remaining part of the operations.

4. A method as claimed in claim 2 wherein the recovering and collection of predetermined quantities of liquids is controlled in dependence or the amount of liquid for said earlier operation available in a reservoir for such liquid.

5. A method as claimed in claim 2 wherein said cycle of operations comprises pre-flushing, washing, rinsing and drying and wherein said predetermined quantities of liquids are recovered and collected from the liquids used for said washing and rinsing operations and are reused for the pre-flushing operation.

6. A method as claimed in claim 5 wherein the temperature of the liquid used for said washing operation is lower than the temperature of the liquid used for said rinsing operation and is higher than the temperature of the liquid used for said pre-flushing operation.

7. A method as claimed in claim 6 wherein the temperature of the liquid used for said pre-flushing operation is at about 35° C and the temperature of the liquid used for said rinsing operation is at about 85° C.

8. A method as claimed in claim 2 wherein said fresh liquid is supplied in heat exchange relationship with liquid stored for said earlier operation.

9. In apparatus for automatic bacteriological cleaning and disinfecting of objects by sequential treatment, the improvement comprising a row of compartments, arranged and designed for such sequential treatment, means for providing liquid-type closure of each compartment relative to surroundings and to each adjacent compartment, tank means for holding treatment fluid separately for each compartment, conveying means for conveying objects sequentially into and out of each compartment, means for conducting and applying liquid to objects in a first compartment from the tank means for holding liquid for that compartment, means for discharging liquid applied to objects in the first compartment so that such liquid does not come in contact with liquid in the tank means for holding fluid for that compartment, means for conducting fresh liquid to tank means for holding treatment liquid for a second compartment, means for conducting and applying the fresh liquid to the objects in a second compartment from the tank means for holding liquid for that compartment, means for discharging liquid applied to objects in the second compartment directly to the tank means for holding liquid for the first compartment, and means for conducting and applying heated air to objects in a final compartment to dry such objects.

10. Apparatus according to claim 9 for automatic bacteriological cleaning and disinfection of objects by sequential treating of the objects comprising conveying means confined to each compartment for moving objects to, through and out of each compartment; means for supplying treatment fluid to each of said compartments; means in each compartment for distributing the fluid over the objects received therein; means for controlled transfer of a predetermined quantity of liquid from at least the second compartment to the tank of the first compartment; and means for supplying fresh liquid to the rest of the liquid for at least said second compartment.

11. An apparatus as claimed in claim 10 wherein said closure means comprise double wall means at each end of each compartment including two wall sections mutually spaced and each arranged for movement in liquid-tight relationship to guide means at the sides of the compartment, and means for moving said double wall means between open and closed position by a substantially vertical movement.

* * * * *

UNITED STATES PATENT AND TRADEMARK OFFICE
CERTIFICATE OF CORRECTION

PATENT NO. : 4,073,663

DATED : February 14, 1978

INVENTOR(S) : LUNDGREN

It is certified that error appears in the above-identified patent and that said Letters Patent are hereby corrected as shown below:

Column 1, line 32, "nosocomical" should read --nosocomial--; line 63, "used" should read --used,--; line 65, "carriage" should read --carriages--. Column 3, line 56, "thereof" should read --thereof,--. Column 4, line 57, "34," should read --34, 44,--. Column 5, line 3, "positions" should read --positions,--; line 5, "surrounding" should read --surroundings--; line 37, "feeding" should read --feeding successive carriages, such as carriage 10, stepwise through--. Column 8, line 17, "switch" should read --switched--. Column 9, line 49, "proceeding" should read --preceding--. Column 10, line 11, "invention" should read --invention,--. Column 11, line 8, "an" should read --an optimum--. Column 13, line 11, "surrounding" should read --surroundings--; line 24, "a predetermined" should read --of predetermined--; line 33, "or" should read --on--.

Signed and Sealed this

Twenty-second Day of May 1979

[SEAL]

Attest:

RUTH C. MASON
Attesting Officer

DONALD W. BANNER
Commissioner of Patents and Trademarks